United States Patent [19]

Saleh

[11] Patent Number: 5,653,977
[45] Date of Patent: Aug. 5, 1997

[54] ANTI-IDIOTYPIC ANTIBODY THAT MIMICS THE GD2 ANTIGEN

[75] Inventor: Mansoor N. Saleh, Birmingham, Ala.

[73] Assignee: UAB Research Foundation, Birmingham, Ala.

[21] Appl. No.: 548,378

[22] Filed: Oct. 23, 1995

Related U.S. Application Data

[63] Continuation of Ser. No. 119,342, Sep. 9, 1993, abandoned.

[51] Int. Cl.$^6$ .......................... C07K 16/42; C12P 21/08; C12N 5/16; C12N 5/28; A61K 39/395

[52] U.S. Cl. ........................ 424/131.1; 424/137.1; 424/138.1; 424/142.1; 435/344.1; 435/327; 435/329; 435/330; 530/387.2; 530/387.5; 530/387.7; 530/388.15

[58] Field of Search ............................ 530/387.2, 388.15, 530/387.5, 387.7; 435/240.27; 424/131.1, 142.1, 137.1, 138.1

[56] References Cited

U.S. PATENT DOCUMENTS 4,918,164  4/1990  Hellstrom et al. .

OTHER PUBLICATIONS

Chattopadhyay et al., Cancer Research 51:6045–6051 (Nov. 15, 1991).
Portoukalian et al., Int. J. Cancer 49:893–899 (1991).
Hamilton et al., Int. J. Cancer 53:566–573 (1993).
Saleh et al., Cancer Research 52:4342–4347 (Aug. 15, 1992).
Chen et al., The Journal of Immunology 147(3):1082–1090 (Aug. 1, 1991).
Chen et al., Cancer Research 51:4790–4797 (Sep. 15, 1991).
Waldmann, Science 252:1657–1602, 1991.
Schlom, IN: "Molecular Foundations of Oncology" Broder Ed., Williams & Wilkins, 1991, pp. 95–134.
Chapman et al., J. Clin Invest 88:186–92 1988.
Saleh et al. Human Antibodies & Hybridomas 3:19–24, 1992.
Kozbor et al. Immunology Today 4:72–79, 1983.
Saleh et al., Proc. Am Assoc Cancer Res. 33:339 Mar. 1992.
Saleh et al. J Immunol. 151:3390 15 Sep. 1993.

*Primary Examiner*—Anthony C. Caputa
*Attorney, Agent, or Firm*—Benjamin Aaron Adler

[57] ABSTRACT

The invention provides an anti-idiotypic monoclonal antibody which elicits an immune response in a mammal against the ganglioside GD2 antigen.

5 Claims, 4 Drawing Sheets

ANTI-IDIOTYPIC ANTIBODY THAT MIMICS THE GD2 ANTIGEN

This is a continuation of application Ser. No. 08/119,342, filed on Sep. 9, 1993, now abandoned.

The invention describes herein was made with government support under Grant NO1 CM97611 from the National Cancer Institute, United States Department of Health and Human Services. The U.S. Government has certain rights in this invention.

BACKGROUND OF THE INVENTION

Gangliosides are sialylated glycosphingolipids which have been implicated as tumor-associated membrane antigens in tumors of neuroectodermal origin (Hakamori and Kannagi, Int. J. Cancer 71:231–251 (1983)). Examples of such gangliosides are GM3, GD3, GM2 and GD2.

The disialoganglioside antigen GD2 consists of a backbone of oligosaccharides flanked by sialic acid and lipid residues (Cheresh, D. A. 1987, Surv. Synth. Pathol. Res. 4:97). The antigen is highly expressed on tumor cells of neuroectodermal origin including melanoma, neuroblastoma, and small cell carcinoma of the lung (Hakomori, S.-I. and R. Kannagi, 1983, J. Natl. Cancer Inst. 71:231; Cheresh, D. A. et al., 1986, Cancer Res. 46:5112; Mujoo, K. et al., 1987, Cancer Res. 47:1098).

Since GD2 has been shown to be highly expressed on most melanoma cells and its expression in normal cells is mostly restricted to the brain, GD2 is a candidate for vaccine development, especially in combination with other gangliosides (Hamilton et al. Int. J. Cancer 53:566–573 (1993)). The GD2 antigen has also been the target of a number of therapeutic monoclonal antibody trials that have shown some in vivo antitumor effects (Saleh, M. N. et al., 1992, Human Antibodies and Hybridomas 3(1):19; Saleh, M. N. et al., 1992, Cancer Res. 52:4342; Cheung, N.-K. V. et al., 1992, J. Clin. Oncol. 10:671).

Although gangliosides would be useful as vaccines, they are difficult to produce. Furthermore, some gangliosides are only weakly immunogenic. Those that are immunogenic may not be found on all tumor cells. In humans, the GD2 antigen is weakly immunogenic and generally induces T cell-independent humoral immune responses (Tai, T. et al, 1985, Int. J. Cancer 35:607; Portoukalian et al., Int. J. Cancer, 49:893–899 (1991)).

An alternative approach to using the actual ganglioside antigen as a vaccine is to use an anti-idiotypic antibody that mimics the antigen and elicits an immune response. Anti-idiotypic antibodies have been studied as potential vaccines against pathogenic organisms (Kennedy, R. C. et al., 1986, Science 232:220; Reagan, K. J. et al., 1983, J. Virol. 48:660; McNamara, M. K. et al., 1984, Science 226:1325; Sachs, D. L. et al., 1982, J. Exp. Med. 155:1108) and malignant tumors (Chen, Z. J. et al., 1991, J. Immunol. 147(3):1082; Dunn, P. L. et al., 1987, J. Immunol. 60:181–187; Herlyn, D. et al., 1987, Proc. Natl. Acad. Sci. USA 84:8055; Chattopadhyay, P. et al., 1991, Cancer Res. 51:3183). In animal studies, murine anti-idiotypic antibodies have demonstrated antigen-specific responses across species (xenogeneic model) (Chapman, P. B. and A. N. Houghton, 1991, J. Clin. Invest. 88:186) and within the same inbred species (syngeneic model) (Gaulton, G. N. et al., 1986, J. Immunol. 137:2930; Chen, Z. J. et al., 1991, J. Immunol. 147(3):1082; Dunn, P. L. et al., 1987, J. Immunol. 60:181–187; Yamamoto, S. et al., J. Natl. Cancer Inst. 82:1757). The ability of "internal image" anti-idiotypic antibodies to function as immunogens in a syngeneic system implies that the unique CDR epitopes of the anti-idiotypic antibody can be seen as foreign even by animals that otherwise share a very similar antibody repertoire.

The ability of a human anti-idiotypic antibody to elicit both a humoral (B cell) and cellular (cell-mediated) immune response would have significant clinical implications because tumor rejection in vivo is primarily mediated by T lymphocytes (Cerrotini, J. C. and K. T. Brunner, 1974, Adv. Immunol. 18:67; Greenberg, P. D., 1991, In Advances in Immunology, vol. 49, F. J. Dixon, ed. Academic Press, Inc., Orlando, Fla., p. 281). Rarely have anti-idiotypic antibody reagents been shown to possess T cell stimulatory (cell-mediated) activity (Chen, Z. J. et al., 1991, J. Immunol. 147(3):1082). Only one human anti-idiotypic antibody that mimics a tumor associated antigen (TAA) (gp72 colorectal carcinoma antigen) and elicits a T cell response in animals (Austin, E. B. et al., 1989, Immunology 67:525) and humans (allogeneic system) has been reported (Robbins, A. R. et al., 1991, Cancer Res. 51:5425).

Attempts are being made to develop ganglioside anti-idiotypic antibodies. A murine anti-idiotypic antibody that mimics the GD3 antigen has been developed and elicits anti-GD3 antibodies in xenogeneic animals (Chapman, P. B. and A. N. Houghton, 1991, J. Clin. Invest. 88:186). Murine anti-idiotypic antibodies that mimic the melanoma-associated high molecular weight antigen have also been developed and, with the exception of one reagent that induces humoral and cellular immune responses (Chen, Z. J. et al., 1991, J. Immunol. 147(3):1082), all induce B cell immune responses only (Chen, Z. J. et al., 1991, Cancer Res. 51:4790; Chattopadhyay, P. et al., 1991, Cancer Res. 51:6045). Clinical trials using these reagents have yet to conclusively demonstrate anti-tumor immunity. Recently, Yamamoto et al. (Yamamoto, S. et al., J. Natl. Cancer Inst. 82:1757) developed a murine anti-idiotypic antibody that mimics the GM3 antigen.

It is advantageous to provide as many as possible immunogenic anti-idiotypic antibodies that mimic gangliosides and serve as their surrogates in generating an immune response. In addition to other gangliosides being studied as potential anti-idiotypic antibodies, GD2, which is present on a majority of neuroectodermal tumors, is another candidate for an immunogenic anti-idiotypic antibody. An attempt to develop an anti-idiotypic antibody that mimics the GD2 antigen and elicits an anti-GD2 immune response was unsuccessful (Anderson, D. R. and R. E. McCoobery, 1992, J. Immunother. 11:267).

The object of this invention is to provide an "internal image" anti-idiotypic antibody that elicits both humoral and cellular anti-GD2 immune responses in mammals. The immune response should be specifically directed at the unique "internal image" idiotopes present on the anti-idiotypic antibody that mimics the GD2 antigen. Such an anti-idiotypic antibody may be utilized as a vaccine against GD2-expressing tumors.

SUMMARY OF THE INVENTION

This invention provides an anti-idiotypic monoclonal antibody which elicits an immune response in a mammal against the ganglioside GD2 antigen.

DETAILED DESCRIPTION OF THE INVENTION

Figure 1:
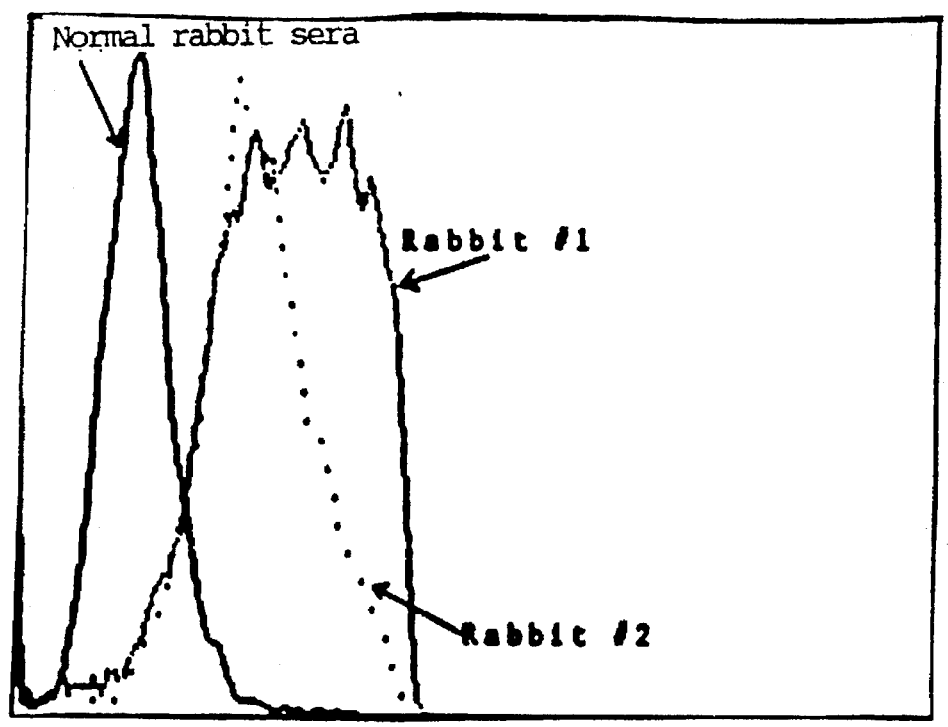
FIG. 1: Binding of rabbit antibody to GD2-positive Mel-21 cells. Mel-21 cell were incubated with normal rabbit sera and sera from rabbits no. 1 and no. 2 obtained after immunization with 4B5. Bound antibody was detected by flow cytometry after incubation with FITC-labeled goat anti-rabbit Ig.

This invention provides an anti-idiotypic monoclonal antibody which elicits an immune response in a mammal, preferably a human, against the ganglioside GD2 antigen. The mammal may also be a rabbit, rat, mouse or other mammal.

An immune response means production of antibodies, i.e. humoral, and/or a cell-mediated response, such as a T-cell response including helper and cytotoxic T cell responses. The immune response is preferably a cell-mediated response, either alone or in combination with a humoral response.

An "antibody" in accordance with the present specification is defined broadly as a protein that specifically binds to an epitope.

The anti-idiotypic antibody of the invention is directed against any anti-GD2 antibody. Anti-GD2 antibodies have been described, such as the murine anti-GD2 monoclonal antibodies 14.18 and 14G2a (Mujoo, K. et al., 1987, Cancer Res. 47:1098; Saleh, M. N. et al., 1992, Cancer Res. 52:4342; Mujoo, K. et al., 1989, Cancer Res. 49:2857) as well as the unrelated anti-GD2 monoclonal antibibody 3F8 (Cheung et al., 1987, J. Clin. Oncol. 5:1430–1440). Anti-GD2 antibodies may be obtained by methods known in the art such as those described below. Preferably, the anti-idiotypic antibody is the monoclonal antibody designated 4B5 produced by the human/mouse heterohybridoma deposited with the ATCC under ATCC Accession No. HB 11447 on Aug. 25, 1993.

Preparation of Antibodies

The polyclonal or, preferably, monoclonal antibodies of the invention may be produced by methods known in the art. These methods include the immunological method described by Kohler and Milstein in Nature 256, 495–497 (1975) and Campbell in "Monoclonal Antibody Technology, The Production and Characterization of Rodent and Human Hybridomas" in Burdon et al., Eds, Laboratory Techniques in Biochemistry and Molecular Biology, Volume 13, Elsevier Science Publishers, Amsterdam (1985); as well as by the recombinant DNA method described by Huse et al in Science 246, 1275–1281 (1989).

One embodiment of the invention provides a cell which produces the anti-idiotypic antibody of the invention. This cell may be any cell, including genetically engineered bacterial cells such as E. coli cells containing DNA to produce the antibody as well as the more typical mammalian cells such as B cells hybridized with murine myeloma cell lines using standard fusion procedures (Kearney, J. F. et al., 1981, Eur. J. Immunol. 11:877).

In a specific embodiment of the invention, a method of producing the 4B5 anti-idiotypic antibody of the invention comprises culturing the human/mouse heterohybridoma designated human 4B5 deposited with the ATCC (ATCC Accession No. HB 11447), and isolating the human 4B5 anti-idiotypic antibodies produced therefrom.

Functional Equivalents of Antibodies

The invention also includes functional equivalents that have binding characteristics and induce immune responses comparable to those of the antibodies described in this specification. Functional equivalents that present the "internal image" epitopes mimicking GD2 may be recombinant or native, and include, for example, single chain, chimerized and humanized antibodies. Chimerized antibodies preferably have constant regions derived substantially or exclusively from human antibody constant regions and variable regions derived substantially or exclusively from the sequence of the variable region from a non-human mammal. Humanized antibodies preferably have constant and variable regions derived substantially or exclusively from human antibody constant and variable regions and CDRs derived substantially or exclusively from a non-human mammal. Suitable non-human mammals include any mammal from which monoclonal antibodies may be made, such as a rabbit, rat, mouse, horse, goat, or primate.

Functional equivalents further include recombinant or native fragments of antibodies that have binding characteristics and induce immune responses comparable to those of the whole antibody. Such fragments may contain one or both Fab fragments or a $F(ab')_2$ fragment, or single chain Fv fragments. Preferably the antibody fragments contain all six complement determining regions of the whole antibody, although fragments containing fewer than all of such regions, such as three, four or five CDRs, may also be functional.

Vaccines

The invention also provides a vaccine composition comprising an effective immunizing amount of the anti-idiotypic antibody of claim A and a pharmaceutically acceptable carrier.

The anti-idiotype antibody of the invention unexpectedly induces an effective immune response when properly presented to the immune system. The immune response preferably inhibits, i.e. prevents, slows or stops, the Growth of cancer cells, or eliminates cancer cells in a mammal. The effective immune response is preferably a B-cell humoral and cell-mediated T-cell response.

The invention provides a method of eliciting an effective immune response against ganglioside GD2 in a mammal comprising administering an effective amount of the anti-idiotypic antibody of the invention to the mammal. The anti-idiotypic antibody preferably is the 4B5 antibody. The mammal is preferably human although may also be a mammal such as a mouse, rat or rabbit.

The vaccine may also comprise a suitable medium. Suitable media include pharmaceutically acceptable carriers, such as phosphate buffered saline solution, liposomes and emulsions.

The vaccine may further comprise pharmaceutically acceptable adjuvants that may enhance the immune response, such as muramyl peptides, lymphokines, such as interferon, interleukin-1 and interleukin-6, or bacterial adjuvants. The adjuvant may comprise suitable particles onto which the anti-idiotypic antibody is adsorbed, such as aluminum oxide particles. These vaccine compositions containing adjuvants may be prepared as is known in the art. An example of a bacterial adjuvant is BCG.

The invention further includes a method of inhibiting the growth of tumors in mammals comprising treating a mammal having precancerous or cancerous cells with an immunologically effective amount of the vaccine of the invention comprising the anti-idiotypic antibody of the invention.

The vaccine is presented to the immune system of the mammal in a form that induces an effective immune response, preferably combined with a pharmaceutically acceptable adjuvant.

The vaccine may be administered to a mammal by methods known in the art. Such methods include, for example, intravenous, intraperitoneal, subcutaneous, intramuscular, topical, or intradermal administration.

Examples of cancerous and precancerous cells associated with expression of GD2 gangliosides include cells of neuroectodermal origin including melanoma, neuroblastoma and small cell carcinoma of the lung. Preferably, the cells are melanoma cells.

Assays for Determining the Level of GD2 Antibody or Antigen in Cells

The level of GD2 antibody or antigen in a sample may be determined by assays known in the art using the anti-idiotypic antibody of the invention. The target GD2 antibody or antigen may be immobilized on a support either indirectly by using an anti-target antibody or directly to the support. Since the anti-idiotypic antibody mimics GD2 and will compete with and thereby inhibit the ability of GD2 to bind with anti-GD2 antibodies, a competitive assay may be used to measure the concentration of GD2 or anti-GD2 antibodies by correlating the level of anti-idiotypic antibody binding to the concentration of GD2 or anti-GD2 antibodies.

A variety of assays are available for detecting proteins with labeled antibodies. In a one-step assay, the target molecule, if it is present, is immobilized and incubated with a labeled anti-idiotypic antibody. The labeled anti-idiotypic antibody binds to the immobilized target molecule. After washing to remove unbound molecules, the sample is assayed for the presence of the label.

In a two-step assay, immobilized target molecule is incubated with an unlabeled anti-idiotypic antibody. The target molecule-unlabeled anti-idiotypic antibody complex, if present, is then bound to a second, labeled antibody that is specific for the unlabeled antibody. The sample is washed and assayed for the presence of the label, as described above.

The choice of marker used to label the antibodies will vary depending upon the application. However, the choice of marker is readily determinable to one skilled in the art. The labeled antibodies may be polyclonal or monoclonal. In a preferred embodiment, the antibody is monoclonal, and is the 4B5 antibody deposited with the ATCC (Accession No. 11447).

Purification Methods

The invention also provides a method of purifying anti-GD2 antibodies in a sample comprising contacting the sample with the GD2 anti-idiotypic antibody of the invention, isolating the complex between GD2 antibodies from the sample and the anti-idiotypic antibody, and recovering the GD2 antibodies from the complex. The anti-idiotypic antibody is preferably immobilized.

This invention is illustrated in the following Experimental Details section. The Experimental Details section is set forth to aid in understanding the invention but are not intended to, and should not be construed to, limit its scope in any way.

EXPERIMENTAL DETAILS

Materials and Methods

Murine anti-GD2 mAb 14G2a

The murine mAb 14G2a is an anti-GD2 antibody that mediates antibody-dependent cytotoxicity and complement-mediated lysis of neuroblastoma and melanoma cell lines in vitro (Mujoo, K. et al., 1987, Cancer Res. 47:1098; Mujoo, K. et al., 1989, Cancer Res. 49:2857). A phase 1 clinical trial of murine 14G2a was conducted in patients with metastatic melanoma. Twelve of 12 patients developed high levels of human anti-mAb including anti-idiotype components (Saleh, M. N. et al., 1992, Cancer Res. 52:4342).

Generation and characterization of human mAbs to murine 14G2a

A melanoma patient received 10 mg of 14G2a in 4 dosages (1,1,4, and 4 mg) on days 1,3,5, and 8. The patient demonstrated a brisk human anti mouse antibody (HAMA) response to 14G2a. Antibody to 14G2a was detected by day 10 with peak values detectable on day 14. The proportion of antibody directed to 14G2a variable region (anti-idiotypic antibody) ranged from 20 to 70% over the first 6 wk.

The patients' MNCs were harvested on day 90 and fused with the nonsecretory murine cell line Ag8. A total of 240 wells were seeded of which 200 (83%) yielded hybrid growth. Supernate form all wells were tested for anti-14G2a reactivity, and Table 1 depicts the assay results of the initial screening of four positive wells. The hybrids in these wells were subcloned, and clones 4B5 and 9B3 were selected for further characterization. Fluorescence microscopic analysis of stained cytospins revealed that clone 4B5 produced a human IgG1 antibody with λ-light chain. The clone 9B3 produced a human IgA-2 antibody with λ-light chain.

Peripheral blood from the patient with metastatic melanoma who was treated with mAb 14G2a was obtained at a time point when human anti-14G2a antibody was detectable in patient serum. MNCs were harvested from peripheral blood by Ficoll-Hypaque (Sigma, St. Louis, Mo.) density gradient centrifugation. The MNC's were hybridized with the murine myeloma cell line P3X.Ag8.653 using standard fusion procedure (Kearney, J. F. et al., 1981, Eur. J. Immunol. 11:877). The cells were subsequently resuspended in RPMI (GIBCO BRL, Grand Island, N.Y.) supplemented with 10% FCS (Hyclone) plus hypoxanthine, aminopterin, thymidine, and seeded at $2 \times 10^5$ MNCs/well. Seven to 10 days later, the wells were supplemented with new media containing only hypoxanthine and thymidine. Resulting hybrids were screened for anti-14G2a reactivity 2–3 wk later. Selected hybridomas were subcloned by limiting dilution, and mAb-secreting hybridomas were expanded in culture.

To measure human anti-14G2a reactivity, the previously described double antigen radiometric assay was used (Saleh, M. N. et al., 1992, Human Antibodies and Hybridomas 3(1):19; Saleh, M. N. et al., 1992, Cancer Res. 52:4342). Briefly, polystyrene beads coated with murine 14G2a were incubated with sample (tissue culture supernate or serum sample when testing patient sera) for 45 min at room temperature on a shaker. After incubation, the beads were washed once with buffer and then incubated with 100 ng of $^{125}$I-labeled 14G2a for 45 min at room temperature on a shaker. After a final wash, the beads transferred to new tubes and the cpm/bead determined on a micromedic γ-counter. Results were expressed either as cpm $^{125}$I-labeled 14G2a bound/100 μl of sample or converted and expressed as ng $^{125}$I-labeled 14G2a bound/ml of sample.

The binding specificity of the human anti-14G2a antibody was assayed by competitive inhibition using the double antigen radiometric assay system. The 14G2a-coated polystyrene bead was incubated with the sample in the presence of excess (30 μg) unlabeled murine 14G2a, chimeric mAb C14.18 (which bears the identical V-region as murine 14G2a and human IgG-1, κ constant regions (Gillies, S. D. et al., 1989, J. Immunol. Methods 125:191; Muller, B. M. et al., 1990, J. Immunol. 144:1382), or polyclonal murine IgG. The ability of excess antigen to inhibit binding of $^{125}$I-labeled 14G2a to the bead compared with binding in the absence of excess antigen was calculated:

$$\% \text{ inhibition} = 1 - \frac{\text{cpm bound in presence of excess antigen}}{\text{cpm bound in absence of excess antigen}} \times 100$$

Murine 14G2a would inhibit both variable and constant region reactivity, whereas murine IgG would be expected to completely inhibit anti-constant region (anti-isotype) reactivity, and excess chimeric C14.18 would only inhibit anti-variable region (anti-idiotypic antibody) reactivity.

The ability of the anti-idiotypic antibody to bind to the antigen-combining site of 14G2a was characterized using a modification of the previously described "mirror image" inhibition assay (LoBuglio, A. F. et al., 1989, Proc. Natl. Acad. Sci. USA 86:4220). The $1 \times 10^6$ Mel-21 cells were incubated with 100 ng of $^{125}$I-14G2a in the presence or absence of 10–100 µl of anti-idiotypic antibody-containing supernate. Cell bound radioactivity was separated from free radiolabel using a Percoll centrifugation step, and $^{125}$I-14G2a bound per $2.5 \times 10^5$ Mel-21 cells was calculated. Inhibition of $^{125}$I-14G2a binding by anti-idiotypic antibody compared with media was calculated.

Determination of Ig subclass and L chain identity of human anti-idiotypic antibody Cytospins of hybridoma cells producing the anti-idiotypic antibody were prepared on glass slides and stained using a previously described method (LoBuglio, A. F. et al., 1989, Proc. Natl. Acad. Sci. USA 86:4220). Briefly, the cytospins were fixed in a mixture of ethanol:glacial acetic acid for 20 minutes at $-20°\pm2°$ C. The slides were washed three times in PBS. The identity of the H chain was determined by staining with an FITC-conjugated mouse anti-human µ-, γ-, or α-antibody (Southern Biotechnology, Birmingham, Ala.), whereas the L chain was identified by staining with FITC-conjugated mouse anti-human κ-or λ-antibody (Southern Biotechnology). Each slide was stained concomitantly for a set of L and H chain combination and analyzed visually by fluorescence microscopy.

Production and purification of anti-idiotypic antibody

A human IgG anti-idiotypic antibody (4B5) was selected for in vivo studies. The producer hybridoma clone was grown in tissue culture using RPMI (GIBCO BRL) media supplemented with 10% FCS. The yield of antibody production in stationary culture was approximately 5 µg/ml. Hybridoma cells were also grown intraperitoneally in scid mice for the production of antibody-containing ascites (Truitt, U. E. et al., 1984, Hybridoma 3:195). The antibody was purified from tissue culture supernate or ascites using a sepharose protein G column (Bird, P., 1984, J. Immunol. Methods 71:87). The IgG was eluted using ammonium acetate (pH 3.5) and immediately adjusted to neutral pH using Tris-HCl. The antibody was dialysed against PBS and the protein content determined using the Lowry method (Lowry, O. H. et al., 1951, J. Biol. Chem. 193:265). The purified antibody was concentrated to approximately 5 mg/ml using a pressure-assisted Diaflo ultrafilter membrane device (Amicon, Beverly, Mass.) after which the final protein concentration was determined.

Immunization with human 4B5 anti-idiotypic antibody

Rabbits were selected for immunization to determine whether the 4B5 anti-idiotypic antibody had immunomimetic properties of GD2 (mirror image anti-idiotypic antibody). Rabbits were selected from these studies because they express gangliosides (including GD2) as self-antigens in a distribution comparable to humans (Iwamori, M. and Y. Nagai, 1981, Biochim. Biophys. Acta. 665:214). The human anti-idiotypic antibody 4B5 was coupled to KLH with 1-ethyl-3-(3-dimethylaminopropyl)carbodiimide hydrochloride using a commercial kit (Pierce no. 77101, 77102, Rockford, Ill). Rabbits were immunized with 500 µg of immunoconjugate in complete Freund's adjuvant on day 0. The animals received the same dose of immunoconjugate in incomplete adjuvant on days 14 and 28 and an intravenous boost of 500 µg native 4B5 on day 42. The animals were bled on day 49. BALB/c mice were similarly immunized with 4B5 coupled to KLH (50 µg/immunization). As control, a separate set of mice was similarly immunized with polyclonal human IgG coupled to KLH.

Testing of sera from rabbits immunized with anti-idiotypic antibody vaccine 4B5

Rabbit sera tested for anti-4B5 reactivity using the double antigen radiometric assay (Saleh, M. N. et al., 1992, Cancer Res. 52:4342). Polystyrene beads were coated with human 4B5 and $^{125}$I-labeled 4B5 was used to detect bound antibody.

Testing of rabbit sera for anti-GD2 activity (Ab-3) was performed by incubating $1.5 \times 10^6$ GD2 expressing Mel-21 tumor cells with 100 µl of sample at 37° C. for 45 min. The cells were then washed three times with PBS containing 1% BSA. The cell pellet was resuspended in 100 µl of buffer to which 100 ng of $^{125}$I-labeled SPA (Boehringer Mannheim, Indianapolis, Ind.) was added (total vol 150 µl ). After a 45-min incubation at room temperature, 50-µl aliquots of the suspension in duplicate were layered onto a 15% Percoll cushion in a microfuge tube and the tubes centrifuged at 600 g for 5 min. The tube tip containing the cell pellet was clamped, cut, and transferred into a γ-counter vial. The cpm/tube tip was determined in micromedic gamma counter. The results were expressed as cpm $^{125}$I-labeled SPA bound/$5 \times 10^5$ Mel-21 cells in each tube tip or converted to molecules of rabbit IgG bound per cell (Shaw, G. M. et al., 1984, Blood 63(1):154). Binding of mouse antibody to Mel-21 cells was similarly assayed using $^{125}$I-labeled SPA.

Binding of rabbit antibody to Mel-21 cells was also independently analyzed by flow cytometry. Thus, cells incubated with pre-and postimmune rabbit sera were washed and subsequently incubated with FITC-conjugated goat anti-rabbit Ig (Southern Biotechnology) at a dilution of 1:1000 in buffer. After a wash step, the cell pellet was resuspended in 1% paraformaldehyde and the cells analyzed on a fluorescent-activated cell analyzer. Binding of mouse antibody to Mel-21 cells was similarly analyzed with FITC-conjugated goat anti-mouse Ig (Southern Biotechnology).

A third assay for anti-GD2 activity in rabbit sera (Ab-3) was to determine the ability of rabbit serum to inhibit the binding of $^{125}$I-labeled murine 14G2a to the GD2-positive Mel-21 cells. This was quantitated by incubating $5 \times 10^5$ Mel-21 cells with 100 ng of $^{125}$I-labeled 14G2 in the presence of 100 µl of the rabbit pre-and postimmunization serum. The amount of radioactivity bound per $2 \times 10^5$ cells were determined using the Percoll centrifugation step described above. The percentage if inhibition was calculated by the formula:

$$\% \text{ inhibition} = 1 - \frac{\text{cpm bound in post-immune sera}}{\text{cpm bound in pre-immune sera}} \times 100$$

This assay determines the degree to which the AB-3 binds to the same epitope on GD2 as 14G2a and therefore behaves like 14G2a (AB'1).

ELISA for detection of anti-GD2 reactivity

Purified GD2 (Sigma, no. G0776) was bound solid phase to polystyrene 96-well ELISA plates as previously described (Chapman, P. B. and A. N. Houghton, 1991, J. Clin. Invest. 88:186). The plates were blocked with PBS containing 1% BSA before incubation with rabbit (100 µl of 1:10 dilution) for 4 hours at room temperature. Bound antibody was detected by goat anti-rabbit Ig conjugated to alkaline phosphatase.

Dot blot assay using purified ganglioside antigen

Purified ganglioside GD2 and GD3 (Sigma) solubilized in ethanol was desiccated in gaseous nitrogen. The ganglioside was subsequently resuspended in distilled water and sonicated before application onto nitrocellulose paper (2 μg/dot). Strips containing blotted antigen were blocked in milk buffer and subsequently incubated with test sera or mAb 14G2a (positive control). Bound antibody was detected with horseradish peroxidase-labeled secondary antibody followed by chromogenic substrate.

DTH response

To assess the ability of human 4B5 anti-idiotypic antibody vaccine to mediate a cellular immune response, rabbits immunized with 4B5 immunoconjugate were shaved on the back and given intradermal inoculum of $1 \times 10^6$ irradiated (10,000 rads) Mel-21 cells or equal numbers of the GD2-negative cell line Ag8 that served as the fusion partner in the generation of 4B5. In a separate set of experiments, two rabbits immunized with native unconjugated 4B5 were given interdermal inoculum of $5 \times 10^6$ irradiated Mel-21 cells or equal numbers of GD2-negative human colorectal carcinoma cells LS-174T (Johnson, V. et al., 1986, Cancer Res. 46:850). In addition, these rabbits also received 100 μg of mAb 4B5 or human IgG1 injected on separate sites. The cutaneous induration at the inoculation site was measured over the next 24 and 48 h.

Binding Specificity

Table II details the binding specificity of mAbs 4B5 and 9B3 demonstrating that 4B5 has specificity for the V-region of murine 14G2a (anti-idiotypic antibody), whereas the 9B3 binds to the constant region of 14G2a (anti-isotype). The lack of complete inhibition of the 9B3 binding probably reflects its high binding affinity.

Inhibition of Binding of GD2 to 14G2a

The human anti-idiotypic antibody 4B5 was further characterized to determine whether it binds to the antigen-combining site of 14G2a. The ability of 4B5 to inhibit the binding of radiolabeled 14G2a to the GD2-positive Mel-21 cells was assessed. Table III depicts the results of such an inhibition experiment. Thus, 100 μl of 4B5 supernate was able to nearly completely inhibit 14G2a binding to Mel-21 cells. In contrast, the anti-constant region antibody 9B3 had no inhibitory property.

Induction of Immune Response

A set of two rabbits were subsequently immunized with 4B5 coupled to KLH to assess whether human anti-idiotypic antibody could mimic the GD2 antigen and therefore induce an anti-GD2 immune response. As shown in Table IV, both rabbits immunized with 4B5 developed large amounts of anti-4B5 reactivity and had to have sera diluted to 1:100 to be in the linear range of the assay.

Figure 2:
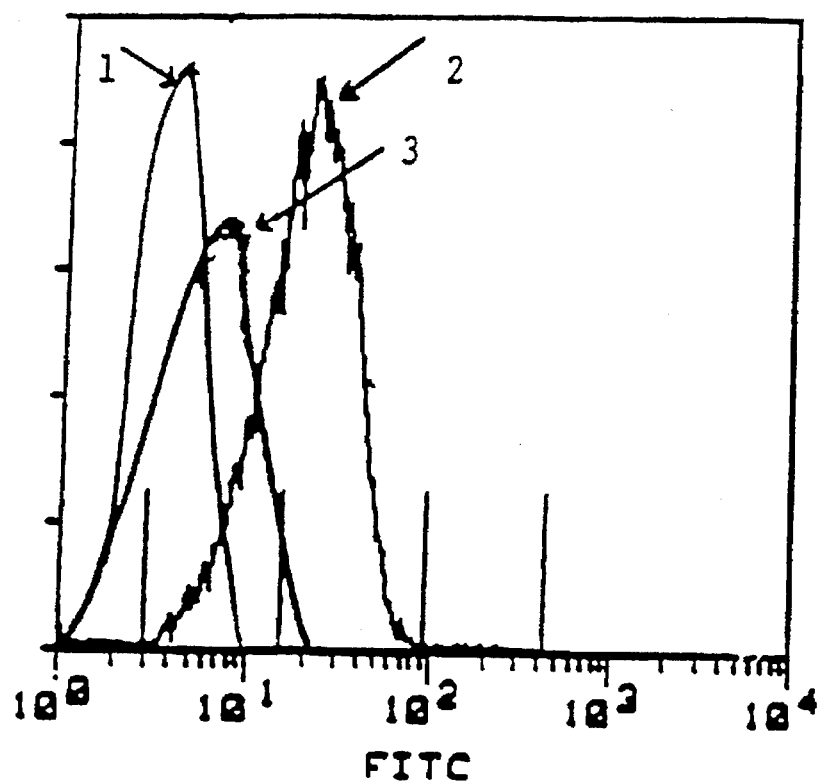
FIG. 2: Binding of mouse sera to GD2-positive Mel-21 cells. Mel-21 cells were incubated with mice sera. Bound antibody was detected by flow cytometry after incubation with FITC-conjugated goat anti-mouse Ig. Lines 1–3 of the graph are as follows: 1. Pre-immune serum; 2. Mouse immunized with anti-Id 4B5; 3. Mouse immunized with irrelevant human antibody.
Figure 3A:
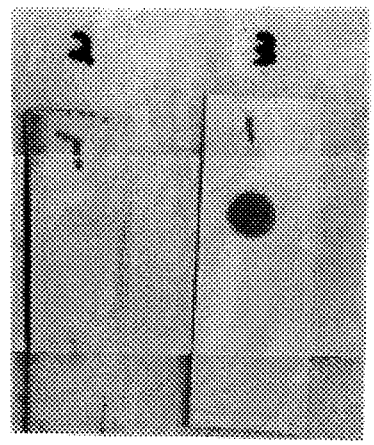
FIG. 3A and B: Dot blot assay using purified GD2 and GD3 ganglioside. Lane 1, rabbit immunized with irrelevant human antibody; lane 2, anti-GD2 mAb 14G2a; lanes 3–6, rabbits immunized with human anti-Id 4B5.
Figure 3B:
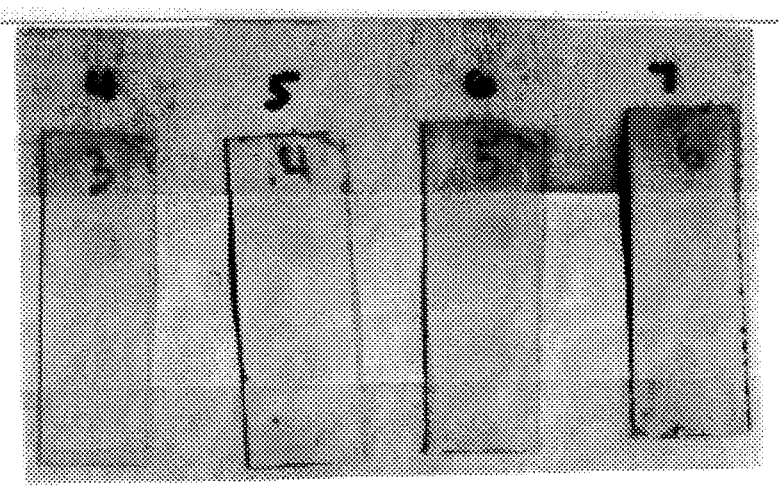

Serum for immunized rabbits also deposited IgG onto the GD2-positive Mel-21 cells as demonstrated using the radiolabeled SPA assay Table V. This finding was confirmed by the marked shift in fluorescence intensity of cells that were incubated with postimmune sera when analyzed by flow cytometry (FIG. 1). Sera from mice immunized with KLH-conjugated 4B5 also deposited IgG onto Mel-21 cells as demonstrated by the radiolabeled SPA assay (Table VI) and flow cytometry (FIG. 2). Control mice similarly immunized with human IgG did not demonstrate such reactivity. Furthermore, antibody from both immunized rabbits also inhibited binding of radiolabeled 14G2a to the GD2-positive Mel-21 cells indicating that the antibody bound to the same (or spatially related) epitope as 14G2a (Table VII). In addition, rabbit sera demonstrated specific GD2 reactivity by solid phase ELISA using purified GD2 antigen (Table VIII). This was further confirmed by dot blot assay. Rabbits immunized with 4B5 demonstrated anti-GD2 (but not anti-GD3) reactivity. Serum from rabbits immunized with an irrelevant human antibody demonstrated no ganglioside reactivity (FIG. 3A and B).

Rabbits previously immunized with 4B5 coupled to KLH underwent skin testing to assess the ability of 4B5 to induce a T cell-mediated cellular immune response. As shown in Table IX, both rabbits developed an erythematous induration at the site of Mel-21 inoculation but no reaction was noted at the Ag8 inoculation site. A separate set of rabbits was immunized with native unconjugated 4B5. The most prominent induration in these rabbits was observed at the 4B5 and Mel-21 inoculation site. Both sites revealed marked erythema and induration. Sites inoculated with human IgG1 and LS-174T cells displayed transient erythema without cutaneous induration Table X.

TABLE I

Double antigen radiometric assay for anti-14G2a in hybridoma supernates

| Sample | cpm bound[a] | ng/ml[b] |
|---|---|---|
| Media | 4761 ± 446 | 17 ± 1.5 |
| Supernate 4B5 | 38,302 ± 2219 | 135 ± 7.8 |
| Supernate 9B3 | 36,385 ± 789 | 128 ± 2.8 |
| Supernate 10A6 | 50,680 ± 3584 | 179 ± 13 |
| Supernate 5D6 | 88,039 ± 4317 | 295 ± 15 |

[a]Mean ± SE of $^{125}$I-14G2a bound to bead per 100 μl sample (duplicate samples).
[b]Results converted to ng of $^{125}$I-14G2a bound/ml supernate (mean ± SE).

TABLE II

Specificity of human mAbs to m-14G2a

| Inhibitor (30 μg) | mAb 4B5 | | mAb 9B3 | |
|---|---|---|---|---|
| | cpm[a] | % Inhibition | cpm[a] | % Inhibition[b] |
| None | 84,479 + 5035 | 0 | 93,178 ± 898 | 0 |
| m-14G2a | 507 ± 27 | 99 | 11,824 ± 1531 | 87 |
| C14.18 | 600 ± 10 | 99 | 93,398 ± 3511 | 0 |
| m-IgG | 84,859 ± 11,631 | 0 | 17,879 ± 1112 | 81 |

[a]cpm of $^{125}$I-14G2a bound/100 μl of sample
[b]Percent inhibition of binding (see Materials and Methods).

TABLE III

Inhibition of $^{125}$I-14G2a binding to Mel-21 by hybridoma supernate[a]

| Samples | cpm/$2.7 \times 10^5$ cells[b] | % Inhibition |
|---|---|---|
| Media | 16,869 ± 379 | — |
| Clone 4B5 | 1429 ± 45 | 92 |
| Clone 9B3 | 16,097 ± 343 | 6 |
| Rabbit anti-14G2a | 7432 ± 154 | 41 |

[a]$1 \times 10^6$ Mel-21 cells were incubated with $^{125}$I-14G2a (186,000 cpm) in the presence or absence of 100 μl hybridoma supernate and radioactivity bound to cells determined (see Materials and Methods).
[b]Mean ± SE of $^{125}$I-14G2a bound per $2.7 \times 10^5$ Mel-21 cells.
[c]A rabbit polyclonal antisera to 14G2a ($F_{AB2}$) containing anti-idiotype reactivity.

TABLE IV

Rabbit antibody response to 4B5 vaccine

| | Anti-4B5 binding | |
|---|---|---|
| | cpm bound[a] | ng/ml[b] |
| Normal rabbit sera (undiluted) | 188 ± 26 | 2 |
| Rabbit no. 1 (1:100) | 10,948 ± 273 | 12,232 |
| Rabbit no. 2 (1:100) | 17,220 ± 407 | 19,240 |

[a]Mean ± SE of $^{125}$I-4B5 bound to bead per 100 μl of a 1:100 dilution of rabbit sera.
[b]Results converted to ng of 4B5 reactivity in 1 ml of rabbit sera (mean ± SE).

TABLE V

Binding of rabbit antibody to GD2-positive MEL-21 cells[a]

| | cpm/5 × 10$^5$ cells[b] | Molecules/cell[c] |
|---|---|---|
| Preimmune sera | 2883 ± 234 | 17,449 ± 1416 |
| Rabbit no. 1 | 48,349 ± 976 | 292,120 ± 5896 |
| Rabbit no. 2 | 31,443 ± 564 | 190,305 ± 3413 |
| Positive control[d] | 89,831 ± 7785 | 543,692 ± 47,117 |

[a]5 × 10$^6$ Mel-21 cells were incubated with 100 μl of pre- or post-immune rabbit sera. After washing, bound rabbit IgG was detected using $^{125}$I -SPA as described in the Materials and Methods section.
[b]Mean ± SE $^{125}$I-SPA bound per 5 × 10$^5$ Mel-21 cells.
[c]Results expressed as molecules of rabbit IgG bound per Mel-21 cell (mean ± SE).
[d]Murine anti-GD2 mAb 14G2a (1 μg/ml).

TABLE VI

Binding of mouse antibody to GD2-positive Mel-21 cells[a]

| | cpm/2 × 10$^5$ cells[b] | Molecules/cell[c] |
|---|---|---|
| Preimmune pooled sera | 1712 ± 11 | 10,357 ± 913 |
| IgG-mouse no. 1 | 1273 ± 11 | 7701 ± 66 |
| IgG-mouse no. 2 | 980 ± 119 | 5929 ± 720 |
| IgG-mouse no. 3 | 1089 ± 44 | 6588 ± 266 |
| 4B5-mouse no. 1 | 3928 ± 38 | 23,764 ± 230 |
| 4B5-mouse no. 2 | 9128 ± 460 | 55,200 ± 2783 |
| 4B5-mouse no. 3 | 6476 ± 326 | 39,179 ± 1972 |

[a]6 × 10$^5$ Mel-21 cells were incubated with 100 μl of pre- or postimmune serum. After washing, bound mouse IgG was detected using $^{125}$I-SPA as described in the Materials and Methods section. The mice were either immunized with nonspecific human IgG coupled to KLH (IgG-mice) or the human anti-idiotypic antibody 4B6 coupled to KLH (4B5-mice).
[b]Mean ± SE cpm $^{125}$I-SPA bound per 2 × 10$^5$ Mel-21 cells.
[c]Results expressed as molecules of rabbit IgG bound per Mel-21 cells (mean ± SE).

TABLE VII

Ability of rabbit antibody to inhibit binding of $^{125}$I-14G2a to MEL-21 cells[a]

| | cpm/2 × 10$^5$ cells[b] | % Inhibition[c] |
|---|---|---|
| Preimmune serum | 14,678 ± 435 | — |
| Rabbit no. 1 | 2238 ± 155 | 86 |
| Rabbit no. 2 | 1781 ± 86 | 89 |

[a]5 × 10$^5$ Mel-21 cells were incubated with 100 ng $^{125}$I-14G2a (157,000 cpm) in the presence of 100 μl of pre- or postimmune rabbit sera. The ability of rabbit antibody to compete with nd inhibit binding of $^{125}$I-14G2a to Mel-21 cells was calculated as described in the Material and Methods section.
[b]Mean ± SE $^{125}$I-14G2a bound per 2 × 10$^5$ Mel-cells.
[c]Percent inhibition of binding in the presence of 100 μl postimmune sera as compared with preimmune sera.

TABLE VIII

GD2 specificity of sera from rabbits immunized with the human anti-idiotypic antibody 4B5

| Rabbit | OD |
|---|---|
| No.1 | |
| Preimmune | 0.04 |
| Day 28 | 0.16 |
| Day 36 | 0.10 |
| Day 61 | 0.08 |
| No.2 | |
| Preimmune | 0.02 |
| Day 28 | 0.13 |
| Day 36 | 0.06 |
| Day 61 | 0.09 |
| 14G2a (positive control) | 1.0 |

Polystyrene ELISA plates were coated with purified GD2 in ethanol (2 μg/ml) and allowed to evaporate. The plates were blocked with borate-saline containing 1% BSA. Test samples (50 μl) were added to wells in duplicate and allowed to incubate 4 hr at room temperature. After washing, bound antibody was detected with goat anti-rabbit Ig conjugated with alkaline phosphate. Wells containing murine 14G2a (positive control) were developed with goat anti-murine Ig conjugated to alkaline phosphatase. OD of the individual wells was determined using an automated plate reader with a 420 nm filter.

TABLE IX

| | DTH response[a] | |
|---|---|---|
| Rabbit | Mel-21 | Ag8 |
| No.1 | | |
| 24 h | 17 × 15 | 0 |
| 48 h | 11 × 14 | 0 |
| No.2 | | |
| 24 h | 9 × 11 | 0 |
| 48 h | 8 × 8 | 0 |

[a]Rabbits immunized with KLH coupled anti-idiotypic antibody 4B5 (see Materials and Methods section) were given intradermal inoculations of 1 × 10$^6$ irradiated Mel-21 or Ag8 cells. The DTH response was assessed as bidimensional measurement in mm of the cutaneous induration at the inoculation site at 24 and 48 hours after injection.

TABLE X

| | DTH response[a] | | | |
|---|---|---|---|---|
| Rabbit | hu-4B5 | hu-IgG | Mel-21 | LS-174T |
| A | | | | |
| 24 h | 14 × 16 | 12 × 10 | 35 × 22 | 4 × 5 |
| 48 h | 24 × 16 | 0 | 36 × 34 | 0 |
| B | | | | |
| 24 h | 12 × 18 | 10 × 5 | 21 × 16 | 0 |
| 48 h | 23 × 14 | 0 | 0 | 0 |

[a]A second set of rabbits (A and B) immunized with native unconjugated 4B5 were given intradermal inoculations of 5 × 10$^6$ irradiated Mel-21 and LS-174T cells and 100 μg 4B5 and human IgG at separate sites. The DTH response was assessed as bidimensional measurement in mm of the cutaneous induration at the inoculation site at 24 h and 48 h after injection.

Supplemental Enablement

The invention as claimed is enabled in accordance with the specification and readily available references and starting materials. Nevertheless, the following hybridoma cell line producing the 4B5 anti-idiotypic antibody of the invention is available at the American Type Culture Collection, 12301 Parklawn Drive, Rockville, Md. 20852 to facilitate the making and using of the invention:

| Hybridoma | Accession No. |
|---|---|
| Human mouse heterohybridoma, Human 4B5 | HB 11447 |

The deposited hybridoma is only intended as a single illustration of one aspect of the invention, and any cell lines which are functionally equivalent are within the scope of the invention.

This deposit was made under the provisions of the Budapest Treaty on the International Recognition of the Deposit of Microorganisms for the Purposes of Patent Procedure and the regulations thereunder (Budapest Treaty). This assures maintenance of a viable culture for 30 years from date of deposit. The organisms will be made available by the ATCC under the terms of the Budapest Treaty, and subject to an agreement between Applicants and ATCC, which assures unrestricted availability upon issuance of the pertinent U.S. patent. Availability of the deposited cell line is not to be construed as a license to practice the invention in contravention of the rights granted under the authority of any government in accordance with its patent laws.

What is claimed is:

1. The anti-idiotypic monoclonal antibody designated 4B5 which elicits an immune response in a mammal against ganglioside GD2 antigen.

2. A hybridoma which produces the anti-idiotypic antibody of claim 1 designated 4B5 hybridoma deposited with the American Type Culture Collection under Accession No. HB 11447.

3. A vaccine composition comprising an amount of the anti-idiotypic antibody of claim 1 effective to immunize against ganglioside GD2 and a pharmaceutically acceptable carrier.

4. A vaccine composition of claim 3 wherein the vaccine also comprises an adjuvant.

5. A method of eliciting an immune response against ganglioside GD2 in a mammal comprising administering to the mammal an effective amount of the anti-idiotypic antibody of claim 1.

* * * * *